United States Patent [19]

Bontemps

[11] Patent Number: 4,850,956
[45] Date of Patent: Jul. 25, 1989

[54] DEVICE DESIGNED FOR SUBCUTANEOUS TRANSFER OF MEDICINAL SUBSTANCES

[76] Inventor: Raymond Bontemps, 5 Avenue de la Grande, Armee, Paris, France, 75008

[21] Appl. No.: 122,367

[22] Filed: Nov. 19, 1987

[30] Foreign Application Priority Data

Dec. 5, 1986 [FR] France .................................. 86 17036

[51] Int. Cl.⁴ .............................................. A61N 1/30
[52] U.S. Cl. ...................................... 604/20; 128/370; 128/795
[58] Field of Search .................................. 128/365–370, 128/639, 795, 798, 802, 803; 604/20

[56] References Cited

U.S. PATENT DOCUMENTS

| | | | |
|---|---|---|---|
| 1,193,018 | 8/1916 | Howard | 128/365 |
| 2,263,205 | 11/1941 | Conrad | 604/20 |
| 4,311,145 | 1/1982 | Esty et al. | 128/303.17 |

FOREIGN PATENT DOCUMENTS 2132892  7/1984  United Kingdom ................... 604/20

Primary Examiner—Max Hindenburg
Assistant Examiner—Randy Citrin
Attorney, Agent, or Firm—Kramer, Brufsky & Cifelli

[57] ABSTRACT

Process for transferring medicine through a patient's skin in which a first pair of electrodes is supported in a first container and the container is filled with the medicine in an electrolytic solution. A patient's foot is immersed in the solution in the first container in contact with the electrodes and a voltage is applied to the electrodes to facilitate the delivery of medicine across the patient's skin. A second pair of electrodes is supported in a second container and the second container is filled with the medicine in an electrolytic solution. Another portion of the patient's skin is exposed to the second pair of electrodes, medicine and electrolyte to receive the medicine. Related apparatus is also disclosed.

11 Claims, 2 Drawing Sheets

DEVICE DESIGNED FOR SUBCUTANEOUS TRANSFER OF MEDICINAL SUBSTANCES

BACKGROUND OF THE INVENTION

The subject of the present invention is a device which subcutaneously transfers medicine.

This electronic device is equipped with large-surface electrodes that are applied by pairs to two distinct parts of the skin of the human body. These electrodes which are immersed in medicinal or cosmetic substances are themselves conductors of electricity and subjected to the electrical output of the voltage generator, and assure the transfer of said substances across the skin.

Different techniques are known at the present time which are designed to cause transfer under the skin of different medicinal or cosmetic substances.

The techniques generally used consist of applying these medicinal substances in the form of an ointment onto previously degreased skin. The application zone is then subjected to a massage so as to assure the penetration of the substance.

One can also use medicinal or cosmetic substances which are frozen in the form of a "stick". These frozen sticks are directly applied onto the skin and the substance penetrates by a cryotherapeutic effect. The latter causes a vasoconstriction followed by a dilation of the pores of the skin, observed when the latter is heated. The substance is absorbed at the time of heating.

We cite finally, within the framework of purely medical treatment, and when it is desired that the products penetrate to the interior of the body, the use of absorption by sublingual means, or even, punctures by intramuscular routes.

All these techniques have numerous disadvantages, in particular:
 a small efficacy
 the use of products concentrated in active substance
 a non-localized action
 a poor specificity.

The electronic device designed for subcutaneous transfer of medicinal substance permits solving these disadvantages, particularly by:
 increasing the efficacy of treatment
 localizing to the nervous system the effect of medicinal substances
 associating with the applied theraputics a relaxing electrical action for the patient
 increasing the frequency and length of treatment without danger to the patient
 making commonplace the use of the device which is the subject of the invention, which may be used directly by the patient without the intervention of a medical specialist.

The electronic device designed for subcutaneous transfer of medicinal substance was built as a result of the following observations:

When an electrical waveform is applied to the two surfaces of an ion-exchange membrane bathed in an electrolyte and simulating the function of a human skin, the migration of specific ions across this membrane toward the cathode compartment is caused.

SUMMARY OF THE INVENTION

When these same electrodes are applied two by two, polarized, onto two parts of human skin, one pair, for example, placed under the sole of the feet bathing in an electrolyte filled with a medicinal substance, and the others applied at the level of the thorax or kidneys, the migration of the medicinal substance toward the central nervous system is caused.

The migration is obtained when the electrodes are subjected to the electrical field of a voltage generator.

In order to avoid applying a continuous electrical field which can evoke nervous irritation, an apolarized wave is used, i.e. having the same electrical sign. The latter, of the type with sawtooth sweeping, assures a modulated current passage causing a cellular vasodilating stimulation. The electrodes placed under the sole of the foot have a voltage rise time of 2.64 seconds, and furnish a current, whose average intensity is 0.5 mA. The return current is 0.08 mA. For the electrodes placed over the thorax or the kidneys, the voltage rise lasts 13.5 seconds for identical intensities. The calculated internal impedance is 15K for the foot currents [and] 20K for currents put out by the electrodes placed over the thorax or kidneys. The voltage furnished by the electrodes placed under the feet imposes a voltage of $-25$ volts to $-50$ volts, while the electrodes attached at the level of the thorax or the kidneys vary their voltage from $-12.5$ volts to $-24$ volts. These variations are controlled by the voltage generator, which brings the potential to zero after each cycle. The value for voltage, intensity of the current, and rate of sweeping can be controlled as a function of the nature of the selected medicinal substances, the physiological characteristics of the patient, and the length of treatment.

From these experiments, the device designed for subcutaneous transfer of medicinal substances, which is the subject of the invention, was constructed, and characterized in that it has a triangular voltage generator with a box fed from the mains with two transformers, diode bridges, a control potentiometer, and transistorized insulating circuits, two motors for the large-surface electrodes, a voltage and sweeping control, an electrolyte storage tank containing the medicinal substance, and a safety circuitbreaker.

The present invention will be better understood by means of the attached drawings which are shown only by way of indicative and non-limiting example of one preferential embodiment selected by the inventor.

DETAILED DESCRIPTION OF THE PREFERRED EMBODIMENTS

Figure 1:
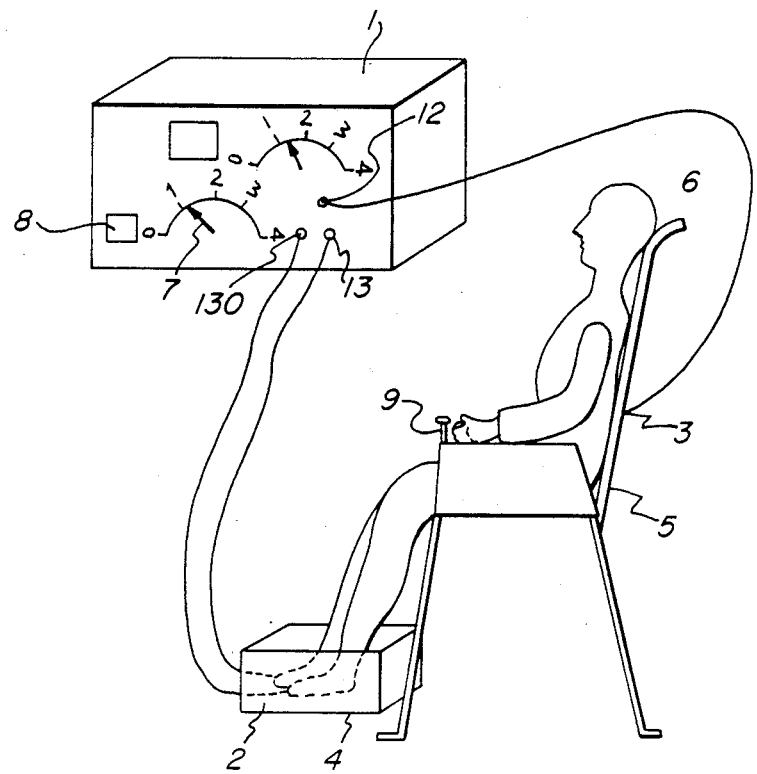
FIG. 1 represents the general organization of the invention.

By referring to FIG. 1 and according to one characteristic of the invention, triangular voltage generator (1) is found placed in the proximity of the patient (6) and supplied by a battery or by the electrical mains. This voltage generator feeds two pairs of electrodes (2) and (3) by two jack plugs. One of these pairs, supporting the sole of the foot is placed in a tank (4) containing the medicinal substance, and the other pair (3) adhere over the kidneys of the patient, has one of its electrodes immersed in the same substance.

The patient (6) is seated on a chair (5), his feet resting on electrodes (2) immersed in tank (4) containing the medicinal substance, and on his back, at the level of the kidneys, is found the pair of electrodes (3) also polarized by the voltage generator.

The patient has available on the arm of the chair a safety switch (9) which stops the electrical waveform instantaneously when this switch is not held in the vertical position, the position of rest always being a position of "stop" of functioning of the electrical generator.

Refering to voltage generator (1), this latter has a control potentiometer (7) of the sweeping amplitude, and a function switch (8).

Figure 2:
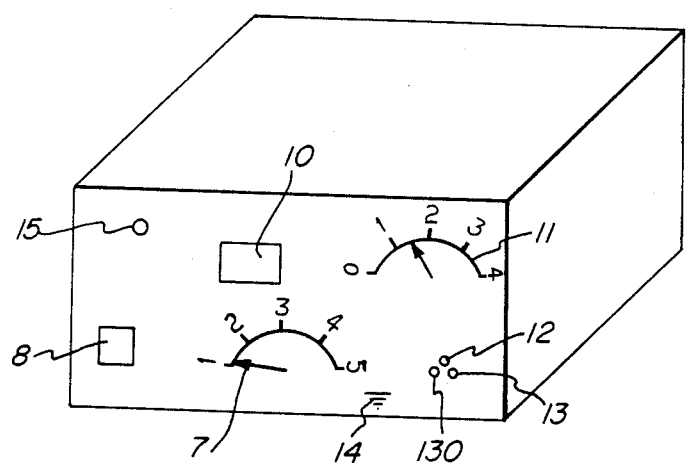
FIG. 2 represents, viewed from the outside, the triangular voltage generator.

In FIG. 2 and according to one important characteristic of the invention, the triangular pulse generator is presented with its external surface toward the front. It is comprised of a box (1) containing the electronics and whose housing is grounded at level (14). Potentiometer (7) permits imposing a sweeping voltage amplitude onto the triangular signals which are generated. Potentiometer (11) is designed to control the rate of sweeping of the signals received by the electrodes. Volt meter (10) permits visualizing the voltage amplitude and the sweeping rate. The jack plugs (12), (130) and (13) constitute signal outlets, contact (12) being connected to the electrodes placed over the kidneys of the patient, contacts (13), (130) being designed to connect the electrodes placed under the feet of the patient. Switch (8) represents the general generator switch and fuse (15) has the task of stopping this generator when the output current intensity continuously exceeds 0.5 mA, or the voltage exceeds 50 volts.

Figure 3:
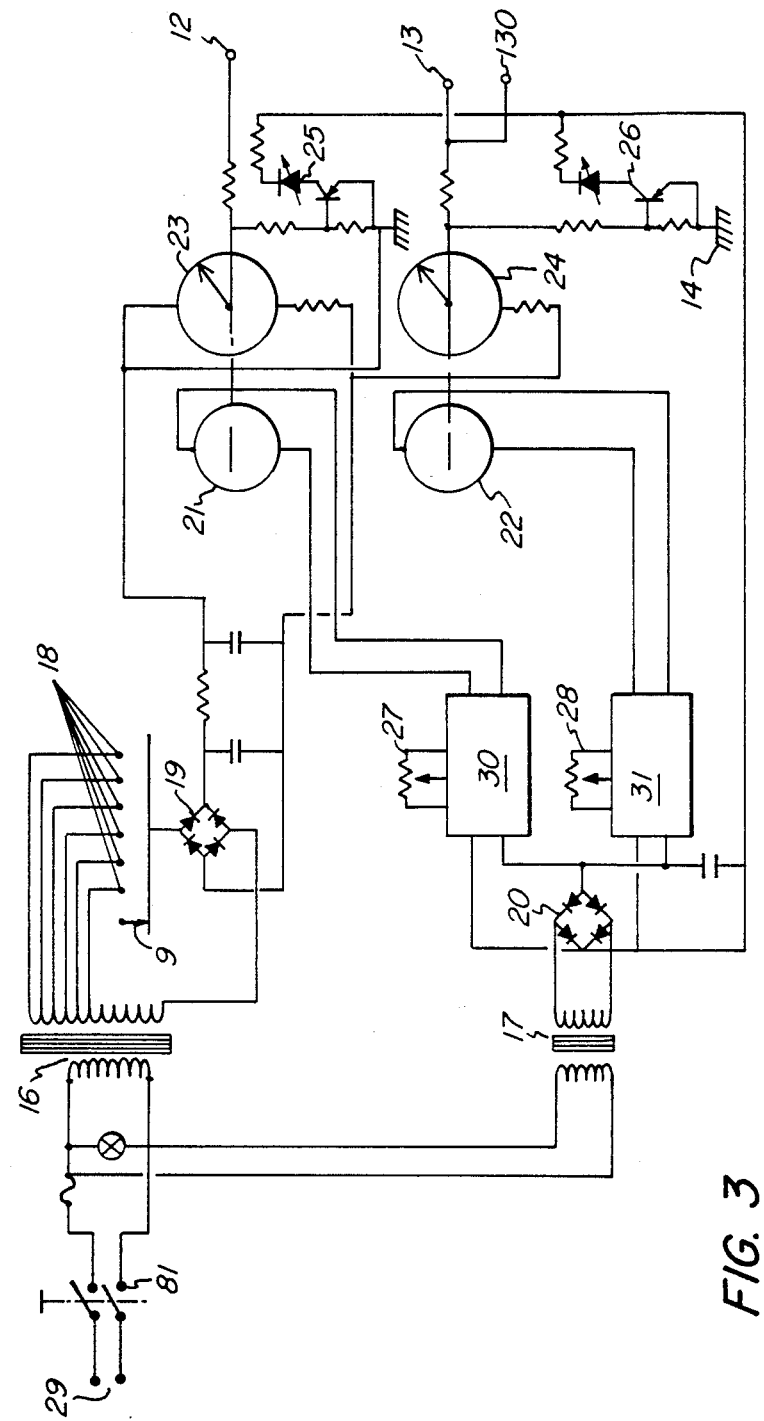
FIG. 3 shows the electronic diagram of the voltage generator.

According to one important characteristic of the invention, FIG. 3 shows the electromechanical assembly for control of the electrical signals from the triangular voltage generator. This electromechanical assembly can easily be replaced by printed circuits, eliminating mechanical control.

Referring to FIG. 3, the voltage generator is fed by an alternating current by the mains at level (29). Relays (81) are designed to trip out the electronics when the output current exceeds 0.5 mA. Transformer (16) adjusts the peak voltage as a function of contacts (18). The current issued from contacts (18) is rectified by diode bridge (19) before being applied to the various electrodes (12), (130) and (13) by way of variable potentiometers (23) and (24). The value of these potentiometers permits adjusting the output current value for each electrode. Variable potentiometers (23) and (24) are activated by motors (21) and (22) during the entire length of the operation and following previously defined sweeping cycles. These motors (21) and (22) are connected to their respective supply (30) and (31) that are controlled by means of variable potentiometers (27) and (28). Supplies (30) and (31) are connected to the mains current by means of diode bridge (20) which rectifies the current issued from transformer (17) directly run off the mains.

The electrical waveform applied to the electrodes is insulated from ground by a circuit comprising transistors (25) and (26) comprised of resistors R6, R7, R10, R11, diodes, and transistors T1 and T2.

The voltage applied to the electrodes depends on the choice of contacts effected at level (18), and the rate of sweeping is controlled by the motor rotation at the level of respective supply sources (27) and (28).

I claim:

1. Apparatus for subcutaneously transferring medicine into a patient's skin, said apparatus comprising:
   container means for holding a solution of medicine and an electrolyte;
   voltage generator means for simultaneously generating multiple periods of a first saw-tooth voltage and multiple periods of a second saw-tooth voltage, said second saw-tooth voltage being different than and nonproportional to said first saw-tooth voltage;
   a first electrode electrically connected to said generator means to receive said first saw-tooth voltage and supported within said container means, said container means including aperture means for receiving a patient's skin in such a manner as to expose said skin to said solution and the voltage of said first electrode; and
   a second electrode electrically connected to said generator means to receive said second saw-tooth voltage and adapted to be exposed to the skin of said patient remote from said first electrode; and wherein:
   said second saw-tooth voltage is substantially always greater than said first saw-tooth voltage such that current flows substantially in one direction only from said second electrode to said first electrode, said first electrode returning current provided by said second electrode.

2. Apparatus as set forth in claim 1 wherein said aperture means is sized to receive a patient's foot, and said first electrode is positioned in said container means to contact said foot.

3. An apparatus as set forth in claim 2 wherein the voltage generator means comprises first and second motors, first and second potentiometers, and first and second voltage sources, said first potentiometer having a voltage input connected to an output of said first voltage source and an output connected to said first electrode and said second potentiometer having a voltage input connected to an output of said second voltage source and an output connected to said second electrode, said first and second motors being connected to wipers of said first and second potentiometers, respectively, and means for driving said motors to repetitively ramp the voltages applied to said first and second electrodes, respectively.

4. An apparatus as set forth in claim 3 further comprising means for controlling the speeds of said first and second motors.

5. An apparatus as set forth in claim 1 further comprising safety circuit breaker means for limiting the maximum electrical voltage which can be applied to said first electrode.

6. An apparatus as set forth in claim 5 wherein the safety circuit breaker means comprises switch means, responsive to manual pressure by the patient, for maintaining the current delivered to said first electrode, whereby the switch in the rest position blocks the delivery of current to said first electrode.

7. An apparatus as set forth in claim 6 wherein the safety circuit breaker means further comprises relay means for tripping off the voltage generator means when the current exceeds a predetermined limit.

8. A process for transferring medicine through a patient's skin, said process comprising the steps of:
   providing a container and a first electrode therein;
   filling the container with medicine in an electrolytic solution;

positioning a first portion of a patient's skin in contact with the solution and exposition to said first electrode;

applying multiple periods of a first saw-tooth voltage waveform to said first electrode while said first electrode is exposed to said first portion of the patient's skin;

positioning a second electrode in exposition to a second, remote portion of the patient's skin; and applying multiple periods of a second, saw-tooth voltage waveform to said second electrode while said second electrode is exposed to said second portion of the patient's skin, said second saw-tooth voltage being different than and nonproportional to said first saw-tooth voltage and both said first and second waveforms being applied simultaneously; and wherein:

said second saw-tooth voltage is substantially always greater than said first saw-tooth voltage such that current flows substantially in one direction only from said second electrode to said first electrode, said first electrode returning current provided by said second electrode.

9. A process as set forth in claim 8 wherein the first portion of the patient's skin is on the patient's foot, and the second portion of the patient's skin is on the patient's torso.

10. A process as set forth in claim 9 wherein said first saw-tooth voltage waveform has a shorter rise time than said second saw-tooth voltage waveform.

11. A process as set forth in claim 9 wherein said first saw-tooth voltage waveform has a greater peak voltage than said second saw-tooth voltage waveform.

* * * * *